United States Patent [19]

Henkin

[11] 4,156,428
[45] May 29, 1979

[54] TRACHEAL TUBE WITH EXPANDABLE CUFF SYSTEM

[76] Inventor: Melvyn L. Henkin, 19640 Greenbriar Dr., Tarzana, Calif. 91356

[21] Appl. No.: 546,744

[22] Filed: Feb. 3, 1975

Related U.S. Application Data

[63] Continuation-in-part of Ser. No. 500,480, Aug. 26, 1974, abandoned.

[51] Int. Cl.² ............................................ A61M 25/00
[52] U.S. Cl. .................................................. 128/351
[58] Field of Search .................. 128/10, 11, 241, 245, 128/246, 349 B, 350 R, 351; 138/30; 128/230–232; 92/92

[56] References Cited

U.S. PATENT DOCUMENTS

| 3,057,347 | 10/1962 | McGee | 128/351 X |
|---|---|---|---|
| 3,173,418 | 3/1965 | Baran | 128/351 |
| 3,322,126 | 5/1967 | Rusch et al. | 128/351 |
| 3,394,705 | 7/1968 | Abramson | 128/241 X |
| 3,407,817 | 10/1968 | Galleher, Jr. | 128/351 |
| 3,599,642 | 8/1971 | Tindel | 128/351 |
| 3,766,927 | 10/1973 | Jackson | 128/351 |
| 3,848,605 | 11/1974 | Harautuneian et al. | 128/351 |
| 3,854,484 | 12/1974 | Jackson | 128/351 |

Primary Examiner—Robert W. Michell
Assistant Examiner—Jeffrey W. Tayon
Attorney, Agent, or Firm—Freilich, Hornbaker, Wasserman, Rosen & Fernandez

[57] ABSTRACT

A cuff system particularly useful with tracheal tubes and the like including an expandable cuff insertable into a patient's trachea for sealing engagement with the trachea wall. The cuff is formed around an elongated tubular member by a flaccid readily deformable non-distensible wall. A liquid reservoir comprised of a flaccid readily deformable wall communicates with the cuff via a filling pipe whose ends respectively open into the reservoir and cuff. The reservoir is mounted in a semi-rigid squeezable protective housing. The cuff system interior volume enclosed by the reservoir, filling pipe, and cuff contains no gas and is supplied with the cuff evacuated and lying against the tubular member and with the reservoir and filling pipe containing a quantity of liquid. A selectively operable valve is provided to control flow through the filling pipe. In use, after intubation of the tracheal tube into the trachea, the valve is opened, the reservoir is elevated above the trachea, and the housing is squeezed to cause the liquid to flow from the reservoir into the cuff thereby expanding the cuff wall toward the tracheal wall. After sufficient liquid has flowed into the cuff to sealingly engage the cuff wall against the tracheal wall, the reservoir is lowered to a desired level above the elevation of the cuff. The valve is then closed. To deflate the cuff prior to extubation, the reservoir is placed below the cuff and the valve is released. The liquid then flows out of the cuff by siphoning action.

16 Claims, 9 Drawing Figures

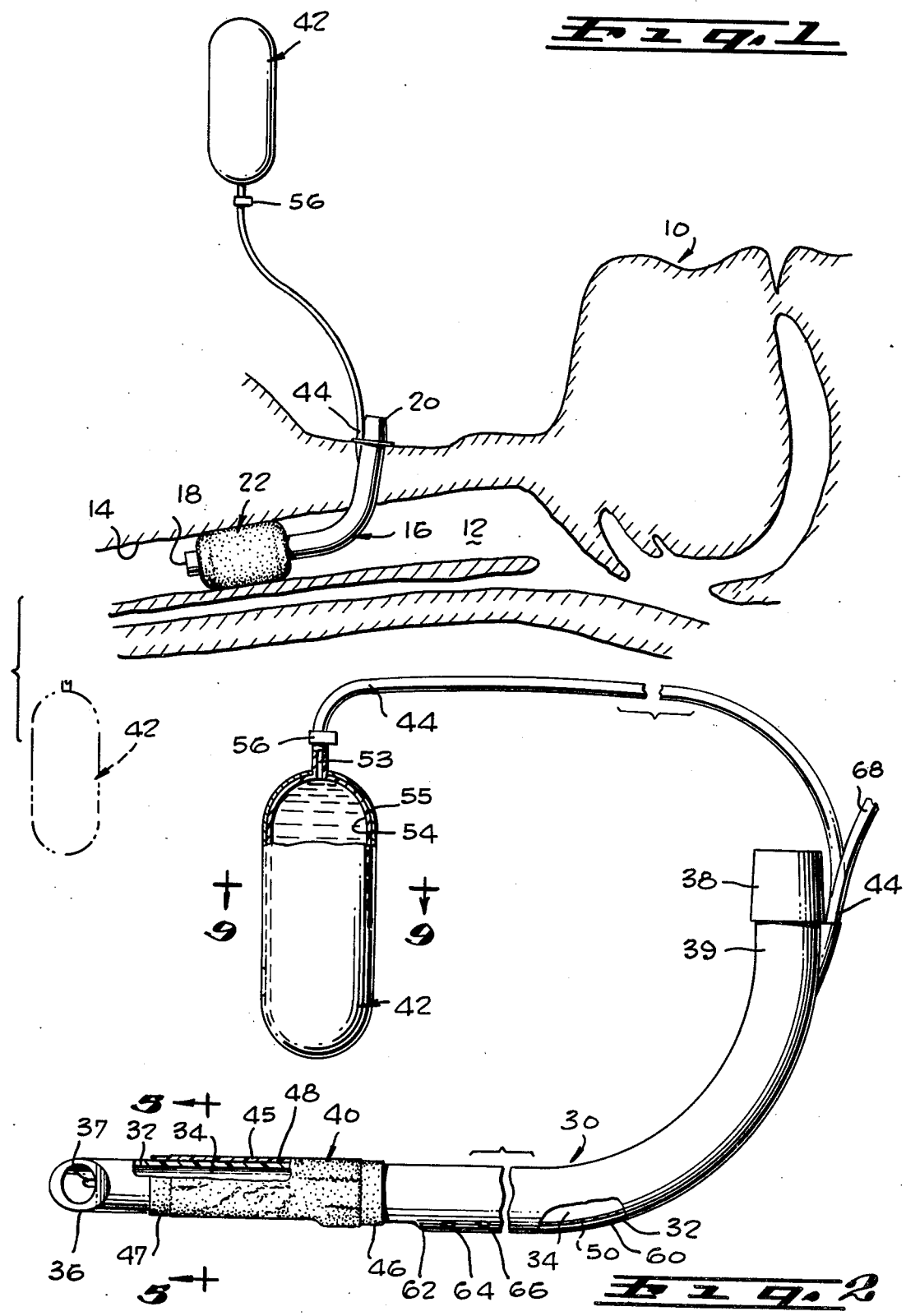

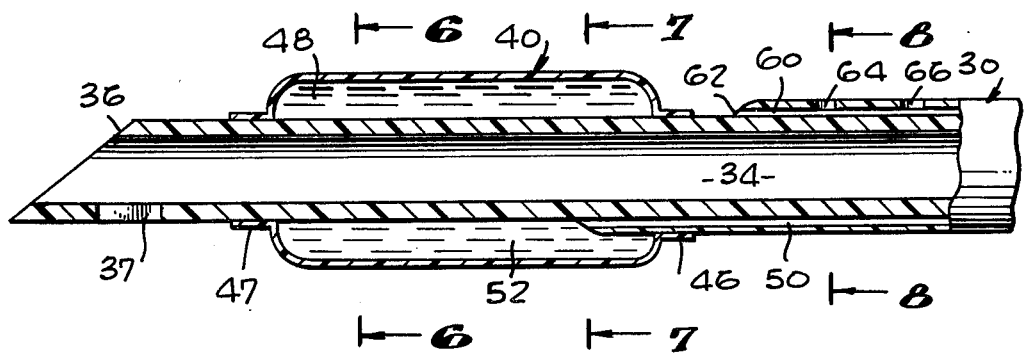
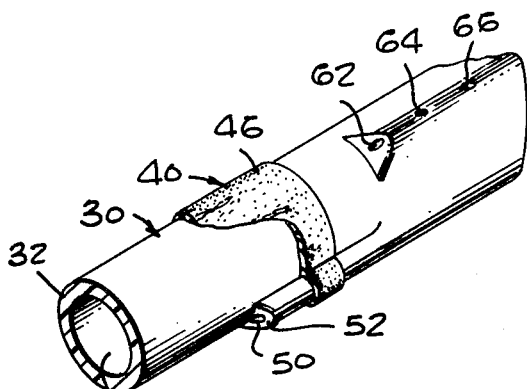
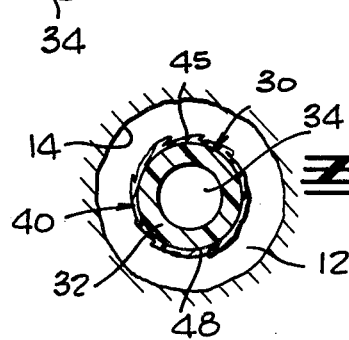
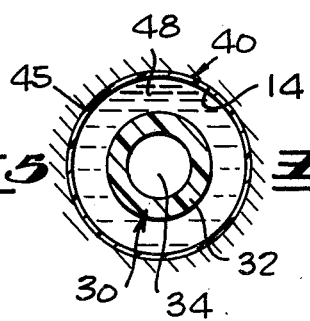
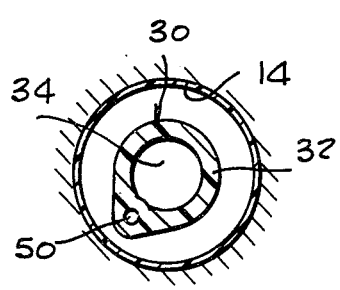
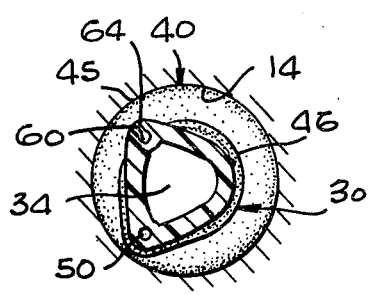
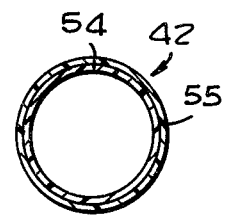

TRACHEAL TUBE WITH EXPANDABLE CUFF SYSTEM

RELATED APPLICATIONS

This application is a continuation-in-part of applicant's parent application, Ser. No. 500,480, filed Aug. 26, 1974 now abandoned.

BACKGROUND OF THE INVENTION

Tracheal tubes (e.g. endotracheal and tracheostomy) are used by physicians for intubation into a patient's trachea for various purposes such as to enable the patient to breathe or to enable intermittent positive pressure ventilation of the respiratory tract. Various tracheal tube configurations are well known in the art, most of which include some form of expandable cuff for sealingly engaging the trachea wall. Typically, the cuff is inflated by room air using a syringe applied to a valve connected to the cuff filling pathway. The cuff is normally inflated to a pressure equal to or above the anticipated interpulmonary pressure to assure that the interpulmonary pressure does not compress the cuff and allow gas leakage out of the trachea. While inadequate pressure to seal the cuff against the trachea wall allows leakage of positive pressure gases, it has been recognized that excessive cuff pressure applied over extended periods may cause damage to the mucosa of the upper trachea; e.g. U.S. Pat. No. 3,640,282; "An Engineering Analysis of Intratracheal Tube Cuffs" by G. E. McGinnis et al, *Anesthesia and Analgesia*, July-August 1971; "The Endotracheal Cuff: A Comparative Study" by P. B. Dobrin et al, *Anesthesia and Analgesia*, May-June 1974.

Applicant's parent application discloses an expandable cuff system useful with tracheal tubes for effecting a seal against the trachea wall. The cuff system is comprised of a liquid reservoir formed by a readily deformable non-elastic wall coupled by a flexible filler pipe to an expandable cuff formed by flaccid readily deformable, non-distensible material. In use, after intubation of the tracheal tube into a patient's trachea, a valve in the filler pipe is opened and the reservoir is elevated above the trachea to cause the liquid to flow via gravity from the reservoir into the cuff thereby expanding the cuff wall against the trachea wall. After the cuff wall seals against the trachea wall, the reservoir is lowered to a level just above the cuff, thereby reducing the hydrostatic head and the pressure exerted by the cuff against the trachea wall. The valve in the filler pipe is then closed to maintain this low sealing pressure. To enable the user to conveniently handle the reservoir without applying pressure to the liquid therein, the reservoir is mounted within a vented rigid housing. A similar structure is disclosed in U.S. Pat. No. 3,766,927 issued to Richard R. Jackson.

Other expandable devices intended for insertion into the human body for purposes of sealing and/or restraining are disclosed in the following U.S. Pat. Nos. 3,087,492; 3,275,001; 3,394,705; 3,401,698; 3,640,282; 3,642,004; 3,625,793; 2,912,981; 3,045,677; 3,528,869; 2,919,697; 3,292,627; 2,896,629; 2,927,584; 3,409,016.

SUMMARY OF THE INVENTION

The present invention is directed to an improved expandable cuff system and method of use thereof for effecting a seal against the wall of a hollow organ, such as the human trachea.

Experience has now shown that although apparatus as taught in applicant's parent application is indeed capable of providing an effective low pressure seal, sole reliance on gravity to induce liquid flow from the reservoir to the cuff is undesirable. More particularly, it has been found that for any reasonable range of dimensions selected, free flow of liquid from the reservoir into the cuff takes several seconds. At best, this delay has proved to be inconvenient in the operating room. More significantly, however, the delay may be unacceptable for certain emergency medical procedures. Still further, it has also been found that creases may form in the flaccid cuff wall during storage or during use in a trachea smaller than the maximum diameter of the cuff and the force attributable to the hydrostatic head may in some cases be insufficient to unfold these creases to provide a satisfactory seal.

In view of the foregoing problems, it is an object of the present invention to provide an improved low pressure cuff system which can be expanded more rapidly and more reliably than the apparatus disclosed in applicant's parent application.

In accordance with an important aspect of the present invention, the liquid reservoir, having a readily deformable wall, is mounted in a semi-rigid vented protective housing which can be squeezed by the user to start or accelerate liquid from from the reservoir to the cuff. Although squeezing the reservoir may produce a pressure in the cuff and against the trachea wall sufficiently high to cause injury to the trachea mucosa if maintained for an extended period, no noticeable injury will occur when an embodiment of the invention is properly used. That is, after the semi-rigid housing is momentarily squeezed to force the liquid from the reservoir into the cuff, the reservoir is lowered to just above the level of the cuff so that the cuff pressure is defined solely by the hydrostatic head. The valve in the filler pipe is then closed to maintain this low pressure.

Although the cuff system in accordance with the invention is disclosed herein primarily in combination with tracheal tubes, it finds important utility in other applications which require the expansion of a cuff or other chamber in a relatively inaccessible location. For example only, the present cuff system is particularly suited for use in Foley-type catheter applications wherein the cuff is expanded after insertion into the body in order to retain the catheter in place.

In accordance with an important feature of the invention, an endotracheal tube is provided including a tubular member having a wall outer surface of substantially triangular cross-section for the purpose, inter alia, of better conforming to the space between the vocal cords than round tubes.

In accordance with a further feature of the invention, an endotracheal tube is provided which incorporates a suction pathway opening immediately above the expandable cuff for enabling material to be suctioned from the patient in the area above the cuff while the tracheal tube is intubated.

BRIEF DESCRIPTION OF THE DRAWINGS

FIG. 1 is a schematic sectional view showing a tracheostomy tube device in accordance with the present invention intubated in a patient;

FIG. 2 is a plan view of an endotracheal tube device in accordance with the present invention showing the cuff in its deflated condition;

FIG. 3 is an enlarged fragmentary view of a portion of the endotracheal tube device of FIG. 2, rotated 90°, and showing the cuff inflated;

FIG. 4 is an isometric view of a portion of a preferred endotracheal tube showing the termination of the filler and suction pipes;

FIG. 5 is a sectional view taken substantially along the plane 5—5 of FIG. 2;

FIGS. 6, 7, 8 are sectional views taken substantially along the planes 6—6, 7—7, 8—8, respectively of FIG. 3; and FIG. 9 is a sectional view taken substantially along the plane 9—9 of FIG. 2.

DESCRIPTION OF THE PREFERRED EMBODIMENT

Attention is now called to FIG. 1 which schematically illustrates a human patient 10 having a trachea 12 defined by trachea wall 14. As is well known, certain medical procedures require the intubation of a tube into the patient's trachea as, for example, to enable the patient to breathe or to enable intermittent positive pressure ventilation of the respiratory tract. Tracheal tube devices for performing such procedures are well known in the art and generally consist of a flexible elongated tubular member 16 having an open lower end 18 and an upper end opening through anesthesia connector 20. In use, the tubular member 16 extends through a surgically formed opening in the patient's neck in the case of a tracheostomy tube device (FIG. 1) in which the connector 20 has an external flange for resting on the patient's neck or through the patient's nose or mouth in the case of an endotracheal tube device (FIG. 2). Such prior art tracheal tube devices are generally provided with an inflatable cuff 22 which, after intubation into the trachea, can be expanded to engage the trachea wall 14 so as to prevent leakage of positive pressure gases around the cuff 22. Typically, the cuff 22 is inflated by room air using a syringe applied to a valve connected to the cuff filing pathway. As previously mentioned, it has now been recognized that excessive and injurious pressures may be produced on the trachea mucosa by such prior art devices even when skillfully employed by the attending physician. The present invention, in one aspect, is directed to an improved cuff system in which the pressure transmitted by the cuff against the trachea wall to maintain a seal is only the minimum pressure required.

Attention is now called to FIG. 2 which illustrates a preferred endotracheal tube embodiment in accordance with the present invention incorporating an expandable cuff system for sealing and retaining a tracheal tube within a patient's trachea. The tracheal tube device of FIG. 2 is comprised of a flexible elongated tubular member 30 having a wall 32 surrounding a central passageway 34. The passageway 34 is open at the first or lower end 36 of the tubular member 30. A side port 37 opens to the passageway 34 through wall 32 proximate to the lower end 36 for assuring ventilation of the left lung. The tubular member 30 is cut obliquely at its lower end 36 to facilitate insertion of member 30 into the trachea. A connector fitting 38 is mounted on the second or upper end 39 of the tubular member 30. The fitting 38 preferably comprises a fifteen millimeter standard anesthesia connector.

In accordance with the present invention, the elongated tubular member 30 is provided with an expandable cuff system generally comprised of an expandable cuff 40, a liquid reservoir 42, and a filler pipe 44 coupling the reservoir 42 to the cuff 40.

The expandable cuff 40 comprises a wall 45 formed of flaccid non-distensible readily deformable material, such as a 40 durometer vinyl (e.g. PIASTISOL, B. F. Goodrich #370E1724), typically 0.001–0.005 inches thick. The wall 45 is mounted around the outside of the elongated tubular member 30 proximate to the lower end 36 thereof. The cuff wall 45 is sealed to the tubular member 30 at first and second points 46 and 47 spaced along the length of the member 30. The cuff wall 45, together with the outer surface of the tubular member wall 32 enclose a variable toroidal volume or chamber 48 therebetween. FIG. 2 illustrates the cuff evacuated with the cuff wall 45 lying against the tubular member 30 and with a minimal variable volume 48. FIG. 3 illustrates the cuff position of the device, rotated 90° with respect to FIG. 2, with the cuff expanded to a maximum variable volume 48.

The filler pipe 44 extends along the length of the tubular member 30 diverging therefrom near the upper end 39. The filler pipe 44 defines a fill passageway 50 therethrough opening at its lower end 52 into the volume 48. The passageway has sufficiently large dimensions (e.g. 0.040 inch diameter or greater) to assure substantially unimpeded liquid flow therethrough. The filler pipe 44 is flexible above the upper end 39 of tubular member 30 and at its upper end 53 opens into the interior volume of the reservoir 42. The reservoir 42 is formed by a wall 54 formed of a readily deformable material such as a 40 durometer vinyl (e.g. PIASTISOL, B. F. Goodrich, #370E1724), typically 0.010 inches thick. The reservoir 42 is mounted within a protective vented housing 55 whose volume can be reduced by manual action of the user to apply pressure to the reservoir 42. The housing 55 is preferably formed of semi-rigid self-restoring wall material such as a 60 durometer vinyl, typically 0.040 inches thick. Use of the semi-rigid material enables a user to handle the housing 55 in a manner to permit him to apply or not apply manual pressure to the reservoir 42, as desired. A manually operable valve mechanism 56, such as a spring clamp, is mounted on the filler pipe 44 proximate to the housing 55 for enabling a user to control flow through the pipe.

It is important to recognize that the cuff system defines a closed total interior volume respectively enclosed by reservoir 42, filler pipe 44, and cuff 40. In accordance with the present invention, the cuff system is supplied to a user with a total interor volume being essentially gas free and containing a noncompressible fluid, preferably a sterile physiologically compatible solution, e.g. normal saline. Preferably, the system is supplied with the cuff 40 evacuated and therefore lying flat against the outer surface of the tubular member 30 and with the quantity of fluid in the system less than that which could distend the reservoir. The valve mechanism 56 is supplied closed with the sterile liquid being contained primarily within the reservoir 42 and filler pipe 44.

In use, the lower end 36 of the tubular member 30 is inserted into the patient's trachea with the cuff 40 deflated as represented in FIG. 2. After the member 30 has been properly inserted into the trachea, the reservoir 42 is elevated to a position above the level of the cuff 40 and the valve 56 on the filler pipe 44 is released. The user may then gently squeeze the housing 55 to start or accelerate the flow of liquid from the reservoir 42 and filler pipe 44 into the evacuated cuff 40. As a consequence, the cuff wall 45 will expand radially to sealingly engage against the trachea wall 14. If pressure is applied to the housing 55, and thus reservoir 42, it should be maintained for only a very short interval, no longer than is required to expand the cuff wall 45 against the trachea wall. After the user releases manual pressure on the housing 55 to enable the housing wall to reassume its original shape, the pressure of the cuff wall 45 against the trachea wall 14 will be determined by the hydrostatic head or height of the reservoir 42 above the cuff 40. After the cuff toroidal volume 48 has expanded to sealingly engage the cuff wall 45 against the trachea wall, the user will then lower the reservoir 42 to a level just above the cuff, thereby reducing the pressure against the trachea wall. This pressure is readily measurable merely by measuring the height of the reservoir above the cuff. The valve 56 is then sealed closed to maintain the measured pressure and the reservoir 42 can then be placed at any convenient location. As a consequence of the foregoing procedure, the cuff can be very quickly expanded into sealing engagement against the trachea wall and any potentially damaging pressure levels are of sufficiently short duration so as to prevent any actual damage.

It should be understood that reference to the cuff as being formed of essentially nondistensible material, refers primarily to the characteristics of the material within the pressure range contemplated. Although the cuff wall 45 may during filling initially exert a pressure against the trachea wall as the cuff toroidal volume 48 expands, this condition lasts for only a short period since the pressure is reduced to the hydrostatic head determined by the reservoir elevation above the cuff when the reservoir 42 is lowered by the user prior to closure of valve 56. Once the cuff 40 is sealed in the trachea with the valve 56 closed, the peak pressure exerted by the cuff wall 45 against the trachea wall 14 will be no greater than the interpulmonary pressure developed in the lungs during subsequent ventilation. The interpulmonary pressure will act against the noncompressible liquid in the cuff which in turn will bear with like pressure against the trachea. Since the liquid in the cuff is incompressible, there is no concern about the interpulmonary pressure compressing the cuff to leak gas out of the trachea. Although the trachea has for simplicity been represented in FIGS. 5 and 6 as having a circular cross-section, it will be recognized that its shape is in fact more irregular and generally more triangular and the cuff essentially conforms to the shape of the trachea as it expands.

It should be appreciated that as the liquid flows out of the reservoir 42 to expand the cuff 40, the atmospheric pressure on the reservoir wall 54 will compress and deflate the reservoir 42. In order to deflate the cuff 40 prior to extubation, the reservoir 42 is placed below the cuff 40 (shown phantom in FIG. 1) and the valve 56 released. The liquid will then flow out of the cuff by siphoning action into the reservoir 42.

In accordance with a significant feature of an endotracheal tube embodiment of the present invention, the outer surface of the tubular member wall 32 has a substantially triangular shape in cross-section with rounded angles, as can be best seen in FIG. 8. The triangular shape more closely conforms to the space between the straight vocal cords than circularly shaped tubes as have been typically employed in the prior art. That is, the straight vocal cords press against the circular outer surfaces of conventional endotracheal tubes with high point contact pressure thereby possibly producing trauma. The line contact of the straight vocal cords against the straight sides of the triangular tubular member in accordance with the present invention provides line contact with associated low unit area pressure. In addition, the line contact between the tubular member and vocal cords provides a better seal than can be achieved with circular tubular members and enables, particularly in certain pediatric situations, for the tube device to sometimes be employed without an inflatable cuff. Further, use of a triangular shaped tubular member makes a larger central passageway area available thus substantially reducing flow resistance in the major length of the tubular member. Also, the triangular shape of the tubular member yields greater resistance to kinking than the currently used circular shape. Additionally, the increased cross-sectional area made available by the triangular cross-section, enables the fill pipe pathway 50 to be formed interiorly of the tubular member structure as shown in FIGS. 7 and 8.

In accordance with a still further feature of the invention, a suction pathway 60 is provided which is also preferably interiorly formed within the tubular member 30 as represented in FIG. 8. The suction pathway 60 opens at one or more locations 62, 64, 66 at different points along the tubular member above the cuff 40. The upper end of the suction pathway 60 extends beyond the upper end 39 of the tubular member 30, and is open at 68. The provision of the suction pathway with the lower openings located above the cuff 40 enables the removal of material which may have passed below the vocal cords during the time the cuff was expanded. Removal of such material prior to extubation of tracheal tube avoids the possibility of such material being aspirated into the patient's lungs when the cuff is deflated.

Embodiments of the invention can be easily and inexpensively fabricated by known techniques. For example, the tubular member 30 can be formed of a suitable plastic material by injection molding or extrusion. The cuff 40 can be formed of a thin plastic membrane having cylindrical ends sealed to the outer surface of tubular member 30 along circumferential areas 46 and 47. Tracheal tube devices in accordance with the invention will, of course, be dimensioned so as to properly conform to the dimensions of the human body. Thus, the tubular member, in the case of an endotracheal tube device, will be on the order of between 6 and 18 inches in length. The major portion of that length, e.g. up to 15 inches, will be of triangular cross-section to fit between the vocal cords, as aforedescribed, with the lower portion, up to about 3 inches being essentially circular as depicted in FIG. 6. The outer diameter of the tubular member should be on the order of 3-14 millimeters. The filler pipe 44 typically would have an iner diameter of about 0.080 inches and be about 12 inches in length beyond the end 39 of the tubular member 30. Although the filler pipe 44 has been disclosed as preferably being formed integrally with the primary tube, it should be recognized that alternatively, the filler pipe can be formed separately.

The cuff diameter should be approximately 1.5-4 times the diameter of the tracheal tube. The quantity of liquid would be about 5-30 cubic centimeters. Typically, the reservoir 42 and protective housing 55 will be about 3 inches long and have outer and inner diameters respectively of about 0.75 inches. Although the protective housing 55 is disclosed as preferably being formed of semi-rigid material, it should be recognized that the important consideration is that the housing be of a configuration such that it can be easily handled by a user without reducing the volume therein and that the user can, when desired, reduce the housing volume to squeeze the reservoir by applying manual pressure.

Tracheal tube apparatus in accordance with the present invention is preferably individually packaged in plastic bags which remain sealed until used. After packaging and prior to shipment, the tracheal tube device, including the liquid within the closed cuff system, is sterilized, by exposing the package to an appropriate source of radiation, such as cobalt.

From the foregoing, it should now be recognized that tracheal tube improvements have been disclosed herein including an expandable cuff system which enables a cuff to be expanded into sealing engagement against the trachea wall without exerting any injurious pressure on the trachea wall. Although the expandable cuff system has been disclosed particularly in combination with tracheal tube devices, it should be recognized that such a system will find utility wherever it is desired to expand a relatively inaccessible chamber, whether or not the chamber is configured as a cuff surrounding a tubular member.

The embodiments of the invention in which an exclusive property or privilege is claimed are defined as follows:

1. A cuff system useful in combination with an elongated member intended for insertion into an opening in the human body, said cuff system including:
   a cuff means adapted to be supported around said elongated member and comprising a wall enclosing a substantially toroidal volume, said wall including an outer portion formed of substantially nondistensible readily deformable material;
   a reservoir means comprising a wall enclosing a volume, said wall being formed of readily deformable material;
   housing means comprising a wall formed of semi-rigid manually deformable material formed around said reservoir means for enabling the selective application of manual pressure therethrough to said reservoir means;
   an elongated pipe having first and second ends respectively opening into said cuff means volume and said reservoir means volume; and
   a quantity of liquid contained within said reservoir means and pipe for flowing therefrom into said cuff means to expand said toroidal volume.

2. The cuff system of claim 1 including valve means selectively operable to enable and prevent liquid flow through said pipe.

3. The cuff system of claim 1 wherein the total interior volume enclosed by said cuff means, said reservoir means and said elongated pipe is essentially free of gas.

4. A system for selectively expanding the volume of an inaccessible chamber, said system comprising:
   a chamber defined by a wall formed of substantially nondistensible readily deformable material enveloping a variable interior volume;
   a reservoir defined by a wall formed of readily deformable material enveloping a variable interior volume;
   a housing mounted around said reservoir formed of semi-rigid material for permitting the selective application of manual pressure therethrough to said reservoir;
   a flexible pipe defining an interior volume and having first and second ends respectively opening into said chamber and reservoir;
   said interior volumes defined by said chamber, reservoir, and pipe being closed and essentially free of gas and containing a quantity of noncompressible fluid whereby said fluid can be caused to flow into said chamber to expand the volume thereof.

5. The system of claim 4 wherein said chamber is substantially toroidally shaped.

6. The system of claim 4 including valve means for selectively opening and closing the fluid flow path through said pipe.

7. A tracheal tube device comprising:
   an elongated tubular member having open first and second ends;
   expandable means mounted on said member proximate to a first end thereof, said expandable means including a cuff formed of substantially nondistensible readily deformable material extending around said member and sealed to the outer surface thereof at first and second points spaced along the length of said member to envelop a variable interior volume of substantially toroidal shape;
   reservoir means defined by a wall enveloping a variable interior volume, said wall being formed of readily deformable material;
   housing means comprising a wall formed of semi-rigid manually deformable material formed around said reservoir means for enabling the selective application of manual pressure therethrough to said reservoir means;
   fill passageway means opening at a first end into said volume enveloped by said cuff and at a second end into said variable volume enveloped by said reservoir means wall; and
   a quantity of liquid contained within the total interior volume defined by said cuff, passageway means and reservoir means, said total interior volume being essentially free of gas.

8. The device of claim 7 wherein said tubular member includes a wall having an outer surface of substantially triangular cross-sectional shape.

9. The device of claim 7 wherein said tubular member includes a wall having an outer surface and wherein a portion of said fill passageway means is formed internally of said tubular member outer wall surface.

10. The device of claim 7 including a connector fitting mounted on said tubular member adjacent said second end thereof.

11. The device of claim 7 including suction passageway means extending along a portion of said tubular member and opening at a first end proximate to said cuff and at a second end proximate to said tubular member second end.

12. The device of claim 11 wherein said tubular member includes a wall having an outer surface and wherein said suction passageway means is formed internally of said tubular member.

13. The device of claim 12 wherein said suction passageway means includes at least one additional opening between first and second open ends thereof.

14. The device of claim 7 including a valve means for selectively opening and closing the liquid flow path through said fill passageway.

15. A tracheostomy tube device suitable for insertion into a patient's trachea through an opening surgically formed in the patient's neck, said device comprising:
- a flexible elongated tubular member having open first and second ends;
- an externally tapered connector fitting mounted on said tubular member second end, said fitting including external flange means for resting on the patient's neck;
- expandable means mounted on said member proximate to a first end thereof, said expandable means including a cuff formed of substantially nondistensible readily deformable material extending around said member and sealed to the outer surface thereof at first and second points spaced along the length of said member to envelop a variable interior volume of substantially toroidal shape;
- reservoir means defined by a wall enveloping a variable interior volume, said wall being formed of readily deformable material;
- housing means formed comprising a wall formed of semi-rigid manually deformable material around said reservoir means for enabling the selective application of manual pressure therethrough to said reservoir means;
- fill passageway means opening at a first end into said volume enveloped by said cuff and at a second end into said variable volume enveloped by said reservoir means wall; and
- a quantity of liquid contained within the total interior volume defined by said cuff, passageway means and reservoir means, said total interior volume being essentially free of gas.

16. An endotracheal tube device suitable for insertion into a patient's trachea through the patient's nose or mouth, said device comprising:
- a flexible elongated tubular member having open first and second ends, said member being cut along a substantially oblique line adjacent said first end to facilitate insertion of said tubular member into a patient's trachea;
- an externally tapered connector fitting mounted on said tubular member second end;
- expandable means mounted on said member proximate to a first end thereof, said expandable means including a cuff formed of substantially nondistensible readily deformable material extending around said member and sealed to the outer surface thereof at first and second points spaced along the length of said member to envelope a variable interior volume of substantially toroidal shape;
- reservoir means defined by a wall enveloping a variable interior volume, said wall being formed of readily deformable material;
- housing means comprising a wall formed of semi-rigid manually deformable material formed around said reservoir means for enabling the selective application of manual pressure therethrough to said reservoir means;
- fill passageway means opening at a first end into said volume enveloped by said cuff and at a second end into said variable volume enveloped by said reservoir means wall; and
- a quantity of liquid contained within the total interior volume defined by said cuff, passageway means and reservoir means, said total interior volume being essentially free of gas.

* * * * *